United States Patent
Halasz et al.

(10) Patent No.: US 11,207,274 B2
(45) Date of Patent: *Dec. 28, 2021

(54) NANOPARTICLES FOR TREATMENT OF POSTERIOR SEGMENT OCULAR DISEASES AND CONDITIONS

(71) Applicant: UNIVERSITY OF SOUTH FLORIDA, Tampa, FL (US)

(72) Inventors: Kathleen Emily-Ann Halasz, Tampa, FL (US); Yashwant V. Pathak, Tampa, FL (US); Vijaykumar Bhadabhai Sutariya, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/020,699

(22) Filed: Sep. 14, 2020

(65) Prior Publication Data
US 2021/0059952 A1 Mar. 4, 2021

Related U.S. Application Data

(63) Continuation of application No. 15/994,079, filed on May 21, 2018, now Pat. No. 10,772,843.

(60) Provisional application No. 62/513,339, filed on May 31, 2017.

(51) Int. Cl.
| | |
|---|---|
| *A61K 9/51* | (2006.01) |
| *A61K 31/573* | (2006.01) |
| *A61K 9/00* | (2006.01) |
| *A61P 27/02* | (2006.01) |
| *A61K 31/7048* | (2006.01) |
| *B82Y 5/00* | (2011.01) |

(52) U.S. Cl.
CPC .......... *A61K 9/5153* (2013.01); *A61K 9/0019* (2013.01); *A61K 9/0048* (2013.01); *A61K 9/5192* (2013.01); *A61K 31/573* (2013.01); *A61P 27/02* (2018.01); *A61K 31/7048* (2013.01); *A61K 2300/00* (2013.01); *B82Y 5/00* (2013.01)

(58) Field of Classification Search
CPC .. A61K 9/5153; A61K 31/573; A61K 9/0048; A61K 9/0019; A61K 9/5192; A61K 2300/00; A61K 31/7048; A61P 27/02; B82Y 5/00
See application file for complete search history.

(56) References Cited

PUBLICATIONS

Smalling, R. et al. "Formulation and Characterization of a Nano-Particle Drug Delivery System Containing Digoxin and Corticosteroids." Poster presented at USF Health Research Day 2017, Feb. 24, 2017.

*Primary Examiner* — Trevor Love
(74) *Attorney, Agent, or Firm* — Quarles & Brady LLP (57) ABSTRACT

The present invention concerns nanoparticles useful for treating posterior segment ocular diseases or conditions, such as macular degeneration and diabetic retinopathy; compositions comprising the nanoparticles; methods for producing the nanoparticles; and methods for treating posterior segment ocular diseases or conditions, comprising administering the nanoparticles or compositions to the ocular posterior segment of an afflicted eye.

20 Claims, 4 Drawing Sheets

NANOPARTICLES FOR TREATMENT OF POSTERIOR SEGMENT OCULAR DISEASES AND CONDITIONS

CROSS-REFERENCE TO RELATED APPLICATION

The present application is a continuation of U.S. patent application Ser. No. 15/994,079, filed May 31, 2018, which claims the benefit of U.S. Provisional Application Ser. No. 62/513,339, filed May 31, 2017, each of which are hereby incorporated by reference herein in their entirety, including any figures, tables, nucleic acid sequences, amino acid sequences, or drawings.

BACKGROUND OF THE INVENTION

Eye disorders and vision loss are conditions that often involve extended direct and indirect costs, which are likely to continue to increase with aging populations and contribute to growing healthcare expenditures. Vision loss in adults over the age of forty is attributable to four major ocular diseases: macular degeneration, diabetic retinopathy, glaucoma, and cataract. Macular degeneration and diabetic retinopathy affect the posterior segment of the eye, while glaucoma and cataract affect the anterior segment.

In macular degeneration, the macula of the retina is damaged by the abnormal growth of blood vessels and central, focused vision is damaged. Lack of nutrient supply for macula and ultraviolet exposure are believed to contribute to the progression. Macular degeneration, also known as age-related macular degeneration (AMD), typically occurs in older people, and is one of the leading causes of blindness in the U.S. Diabetic retinopathy is similarly associated with new, abnormal blood vessels bleeding into the retina and vitreous. Therapeutic interventions for posterior segment ocular diseases involving delivery of agents to the posterior of the eye are limited due to the physiological barriers of the eye.

BRIEF SUMMARY OF THE INVENTION

The present invention concerns nanoparticles; compositions comprising the nanoparticles; methods for producing the nanoparticles; and methods for treating posterior segment ocular diseases or conditions, such as macular degeneration and diabetic retinopathy, comprising administering the nanoparticles or compositions to the ocular posterior segment of an afflicted eye.

Figure 1:
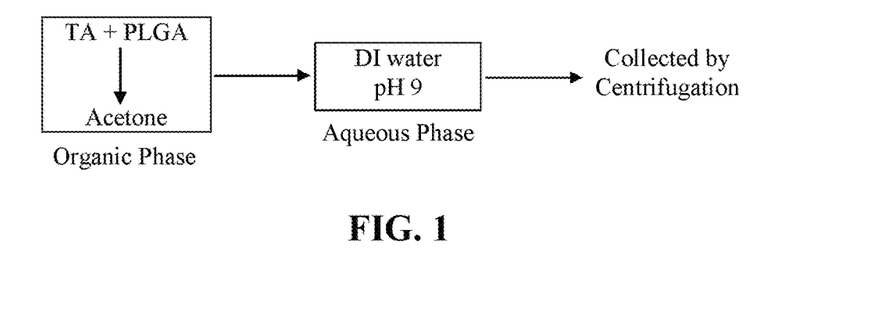
FIG. 1 shows the initial steps of a production scheme for an embodiment of nanoparticles of the invention, depicting production of nanoparticles with a first biologically active agent encapsulated therein, using nanoprecipitation. The first biologically active agent (e.g., triamcinolone (TA)), one or more polymers (e.g., PLGA), one or more solvents (e.g., acetone), and optionally one or more surfactants are mixed to make an organic phase, wherein the organic phase is a solution or dispersion. Water is mixed with one or more acids or one or more bases, and optionally one or more surfactants, to make a first aqueous phase, and the organic phase is mixed with the first aqueous phase to make a colloidal suspension of nanoparticles. At this point in the process, the nanoparticles comprise a core of the first biologically active agent encapsulated by a membrane of the one or more polymers. The nanoparticles may then be isolated or collected from the colloidal suspension, e.g., by centrifugation. Following production of the nanoparticles with the first biologically active agent encapsulated therein, a second biologically active agent can be incorporated by mixing the second biologically active agent with water to make a second aqueous phase, and mixing the nanoparticles with the second aqueous phase to make the nanoparticles (not shown in FIG. 1). Each nanoparticle comprises a core of the first biologically active agent encapsulated by a membrane of the one or more polymers and the second biologically active agent adhering to an outside surface of the membrane of the one or more polymers.

In one embodiment, triamcinolone (TA) nanoparticles (NPs) were prepared by nanoprecipitation with PLGA in acetone (in the organic phase) as well as deionized (DI) water with a pH of 9 and collected through utilization of centrifugation. A schema with these steps is shown in FIG. 1. The collected NPs were then suspended within a 1 mg/mL solution of Digoxin (DIG). Using the same method, blank nanoparticles were also prepared without the drug (digoxin) combination.

DETAILED DESCRIPTION OF THE INVENTION

Recent studies have found that triamcinolone acetonide (TA) and loteprednol etabonate (LE) suppress secretion of the inflammatory cytokine, VEGF. Digoxin (DIG) has been reported to suppress hypoxia induced factor (HIF). A combined system with the ability to suppress both VEGF and HIF may have enhanced benefit in the treatment of posterior segment ocular diseases or conditions such as age-associated macular degeneration (AMD). The inventors treated retinal cells overexpressing VEGF and HIF with nanoparticles containing DIG and corticosteroids, and the suppression was measured via ELISA. These nanoparticles were compared to solutions and the results from each were compared. Through the utilization of nanoparticle drug delivery systems one may deliver a sustained drug release, decreasing the frequency of injections and increasing patient comfort and compliance.

An aspect of the concerns a nanoparticle, comprising a core of a first biologically active agent encapsulated by a membrane of one or more polymers and a second biologically active agent adhering to an outside surface of the membrane of the one or more polymers.

The biologically active agents may be any molecules useful for the intended purpose of the nanoparticles. For example, the biologically active agents may be small organic molecules such as drugs.

When intended for the treatment of a posterior segment ocular disease or condition, for example, the first biologically active agent encapsulated by the polymer membrane may comprise an immunosuppressive agent that suppresses vascular endothelial growth factor (VEGF), and the second biologically active agent may comprise an agent that suppresses hypoxia induced factor (HIF), such as HIF-1; or vice-versa, the second biologically active agent may comprise an immunosuppressive agent that suppresses vascular endothelial growth factor (VEGF), and the first biologically active agent encapsulated by the polymer membrane may comprise an agent that suppresses hypoxia induced factor (HIF), such as HIF-1.

In some embodiments, the immunosuppressive agent comprises a corticosteroid such as triamcinolone or a derivative thereof. In some embodiments, the corticosteroid comprises triamcinolone acetonide or a pharmaceutically acceptable salt thereof. In some embodiments, the immunosuppressive agent comprises loteprednol etabonate or a pharmaceutically acceptable salt thereof. In some embodiments, the agent that suppresses HIP (HIF inhibitor) comprises digoxin or a pharmaceutically acceptable salt thereof.

In some embodiments, the HIF inhibitor comprises a *digitalis* derivative having the chemical structure of Figure I, or a pharmaceutically acceptable salt thereof.

In some embodiments, the immunosuppressive agent comprises a corticosteroid having the chemical structure of Formula II, or a pharmaceutically acceptable salt thereof.

Formulas I and II:

(Formula I)

(Formula II)

where $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, and $R^{21}$ can independently be selected from the group: H; F; Cl; Br; I; OH; CN; $(C_{1-4})$alkyl, such as methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers; alkynyl; aralkyl; alkaryl; halogenated alkyl; heteroalkyl; aryl; heterocyclyl; cycloalkyl; cycloalkenyl; cycloalkynyl; hydroxyalkyl; aminoalkyl; amino; alkylamino; arylamino; dialkylamino; alkylarylamino; diarylamino; acylamino; hydroxyl; thiol; thioalkyl; alkoxy; alkylthio; alkoxyalkyl; aryloxy; arylalkoxy; acyloxy; nitro; carbamoyl; trifluoromethyl; phenoxy; benzyloxy; phosphonic acid; phosphate ester; sulfonic acid (—$SO_3H$); sulfonate ester; sulfonamide; alkaryl; arylalkyl; carbamate; amino; alkylamino; arylamino; dialkylamino; alkylarylamino; diarylamino; alkylthio; heteroalkyl; alkyltriphenylphosphonium; heterocyclyl; ketone (=O);

ether (—$OR^{22}$); and ester (—$COOR^{23}$ and —$OC(=O)R^{23}$); where $R^9$ and $R^{10}$ can be a double bound within the cyclohexane ring;
where $R^{15}$ and $R^{16}$ can be bonded together to form a four-, five-, or six-membered heterocyclyl, cycloalkenyl, or cycloalkyl, such as where $R^{18}$ and $R^{19}$ can be a double bound within the cyclohexane ring; and
where $R^{22}$ and $R^{23}$ can be independently selected from the group: a $(C_{1-4})$alkyl, such as methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers; and alkynyl.

In Formula I, the compound is digoxin when: $R^1$=OH; $R^2$=OH; $R^3$=OH; $R^4$=OH; $R^5$=OH and $R^7$=OH.
In Formula I, the compound is digitoxin when: $R^1$=OH; $R^2$=OH; $R^3$=OH; $R^4$=OH; $R^5$=H and $R^7$=OH.

In Formula II, the compound is triamcinolone when: $R^8$=H; $R^9$ and $R^{10}$=double bond; $R^{11}$=H; $R^{12}$=OH; $R^{13}$=ketone (=O); $R^{14}$=OH; $R^{15}$=OH; $R^{16}$=OH; $R^{17}$=F; $R^{18}$ and $R^{19}$=double bond; $R^{20}$=H; and $R^{21}$=ketone (=O).

In Formula II, the compound is triamcinolone acetonide when: $R^8$=H; $R^9$ and $R^{10}$=double bond; $R^{11}$=H; $R^{12}$=OH; $R^{13}$=ketone (=O); $R^{14}$=OH; $R^{15}$ and $R^{17}$=F; $R^{18}$ and $R^{19}$=double bond; $R^{20}$=H; and $R^{21}$=ketone (=O).

In Formula II, the compound is hydrocortisone when: $R^8$=H; $R^9$=H; $R^{10}$=H; $R^{11}$=H; $R^{12}$=OH; $R^{13}$=ketone (=O); $R^{14}$=OH; $R^{15}$=OH; $R^{16}$=H; $R^{17}$=H; $R^{18}$ and $R^{19}$=double bond; $R^{20}$=H; and $R^{21}$=ketone (=O).

Typically, the one or more polymers are biocompatible and biodegradable. Exemplary biocompatible polymers that may be used to produce the nanoparticles of the invention include, but are not limited to, a poly-lactic acid (PLA), poly-glycolic acid (PGA), poly-lactide-co-glycolide (PLGA), polyesters, poly(ortho ester), poly(phosphazine), poly(phosphate ester), polycaprolactone, gelatin, collagen, fibronectin, keratin, polyaspartic acid, alginate, cellulose, chitosan, chitin, hyaluronic acid, pectin, polyhydroxylkanoates, dextrans, and polyanhydrides, polyethylene oxide (PEO), poly(ethylene glycol) (PEG), triblock copolymers, polylysine, any derivatives thereof and any combinations thereof.

For example, the one or more polymers are poly(lactic-co-glycolic acid) (PLGA), poly lactic acid (PLA), poly caprolactone (PCL), or a combination of two or more of the foregoing may be used to produce the nanoparticles.

Another aspect of the invention concerns a composition useful for carrying out the methods of treatment of the invention. In some embodiments, the composition comprises nanoparticles of the invention disclosed herein; and a pharmaceutically acceptable carrier or diluent. The composition has a viscosity appropriate for its route of administration. The composition may be a fluid that may be administered by injection or dropwise. The composition may be a gel and/or form a part of an ocular implant. In some embodiments, the composition is an injectable fluid that may be administered by intravitreal injection.

Typically, the nanoparticles will be in suspension and the composition comprising the nanoparticles will be within a viscosity range that supports syringability, e.g., intravitreal injection. In some embodiments, a viscosity-modulating component can be present in an effective amount in modulating the viscosity of the composition. In some embodiments, increasing the viscosity of the compositions to values in excess of the viscosity of water (1 centipoise) can allow more effective placement, e.g., injection, of the composition into the posterior segment of an eye. In other embodiments, a viscosity-modulating component can include a shear thinning component, which, when present in the composition, can reduce the viscosity of the composition under a high shear condition as the composition is passed through a narrow space, such as a 27-gauge needle, and injected into the posterior segment of an eye, but the composition can regain its pre-injection viscosity after the passage through the injection needle.

The composition may be formed into a gel implant in vitro for administration to, or in the vicinity of, the eye.

Another aspect of the invention is a method for treating a posterior segment ocular disease or condition in an eye of a subject, comprising administering nanoparticles disclosed herein to the ocular posterior segment of the eye. In some embodiments, the posterior segment ocular disease is macular degeneration (wet or dry) or diabetic retinopathy.

In some embodiments, the posterior ocular condition that may be treated with the nanoparticles involves a posterior segment of an eye, such as choroid or sclera (in a position posterior to a plane through the posterior wall of the lens capsule), vitreous humor, vitreous chamber, retina, optic nerve (including the optic disc), and blood vessels and nerve which vascularize or innervate a posterior ocular region or site. Examples of posterior ocular conditions that may be treated include, but are not limited to, macular degeneration (such as non-exudative age related macular degeneration and exudative age related macular degeneration); macular hole; light, radiation or thermal damage to a posterior ocular tissue; choroidal neovascularization; acute macular neuroretinopathy; macular edema (such as cystoid macular edema and diabetic macular edema); Behcet's disease, retinal disorders, diabetic retinopathy (including proliferative diabetic retinopathy); retinal arterial occlusive disease; central retinal vein occlusion; uveitic retinal disease; retinal detachment; ocular trauma which affects a posterior ocular site; a posterior ocular condition caused by or influenced by an ocular laser treatment; posterior ocular conditions caused by or influenced by a photodynamic therapy; photocoagulation; radiation retinopathy; epiretinal membrane disorders; branch retinal vein occlusion; anterior ischemic optic neuropathy; non-retinopathy diabetic retinal dysfunction, and retinitis pigmentosa. In some embodiments, an ocular condition to be treated is age-related macular degeneration.

The nanoparticles may be administered within a composition comprising the nanoparticles and a pharmaceutically acceptable carrier or diluent.

The nanoparticles and compositions comprising them may be administered by any route that results in delivery of the nanoparticles and/or their biologically active agents to the intended site of action (posterior tissue of the eye). In some embodiments of the treatment method, the nanoparticles or composition is administered by intravitreal injection.

Another aspect of the invention concerns a method for producing a nanoparticle, which may be used in the compositions and methods of the invention, the production method comprising:

mixing a first biologically active agent, one or more polymers, one or more solvents, and optionally one or more surfactants to make an organic phase, wherein the organic phase is a solution or dispersion;

mixing water with one or more acids or one or more bases and optionally one or more surfactants to make a first aqueous phase, mixing the organic phase with the first aqueous phase to make a colloidal suspension of nanoparticles; wherein the nanoparticles comprise a core of the first biologically active agent encapsulated by a membrane of the one or more polymers;

isolating the nanoparticles from the colloidal suspension;

mixing a second biologically active agent with water to make a second aqueous phase, and mixing the nanoparticles with the second aqueous phase to make the nanoparticle, wherein the nanoparticle comprises a core of the first biologically active agent encapsulated by a membrane of the one or more polymers, and the second biologically active agent adhering to an outside surface of the membrane of the one or more polymers.

Other solvents that may be used in place of acetone include, but are not limited to, dichloromethane, acetonitrile and methanol.

In some embodiments the one or more polymers are biocompatible and biodegradable. For example, poly(lactic-co-glycolic acid) (PLGA), poly lactic acid (PLA), poly caprolactone (PCL), or a combination of two or more of the foregoing may be used to produce the nanoparticles.

In some embodiments, the nanoparticle has an average diameter of about 100 to 200 nm. In some embodiments, the nanoparticle has an average diameter of about 114 nm. In some embodiments, the nanoparticle has an average diameter of about 173-174 nm.

In some embodiments, the nanoparticle has a polydispersity index (PI) of about 0.334. In some embodiments, the nanoparticle has a PI of about 0.125.

In some embodiments, the first biologically active agent comprises an immunosuppressive agent that suppresses vascular endothelial growth factor (VEGF), and the second biologically active agent may comprise an agent that suppresses hypoxia induced factor (HIF). In some embodiments, the immunosuppressive agent comprises a corticosteroid such as triamcinolone or a derivative thereof. In some embodiments, the corticosteroid comprises triamcinolone acetonide or a pharmaceutically acceptable salt thereof. In some embodiments, the first biologically active agent comprises loteprednol etabonate or a pharmaceutically acceptable salt thereof. In some embodiments, the second biologically active agent (HIF inhibitor) comprises digoxin or a pharmaceutically acceptable salt thereof.

Nanoparticles may be collected or isolated using methods known in the art such as centrifugation.

In some embodiments, the nanoparticle releases about 75% to about 85% of the first biologically active agent in 20 hours, and releases about 15% to about 25% of the second biologically active agent in 20 hours.

In some embodiments of the nanoparticles, compositions and methods of the invention, the first biologically active agent is a small molecule drug (a low molecule weight (less than 900 daltons) organic compound). In some embodiments, the second biologically active agent is a small molecule drug. In some embodiments, both the first and second biologically active compounds are small molecule drugs.

Optionally, additionally biologically active agents can be incorporated into or onto the nanoparticles of the invention, either encapsulated within the polymer membrane or adhered to the membrane, or both. For example, other agents useful for treatment of posterior segment ocular conditions may be included.

The compositions for ocular administration described herein can be formulated for various target sites of administration in an eye, e.g., but not limited to, lens, sclera, conjunctiva, aqueous humor, ciliary muscle, and vitreous humor. In some embodiments, the composition is formulated to be an injectable composition, e.g., for intravitreal administration.

In some embodiments, the nanoparticles can be further embedded in a solid substrate and/or a biomaterial, e.g., to prolong and/or localize the release of a therapeutic agent to a target site over a period of time. Examples of a solid substrate in which the nanoparticles can be embedded include, but are not limited to, a tablet, a capsule, a microchip, a hydrogel, a mat, a film, a fiber, an ocular delivery device, an implant, a coating, and any combinations thereof.

The term "therapeutically effective amount" as used herein refers to an amount of a therapeutic agent (e.g., nanoparticles or payload of biologically active agents on the nanoparticles) which is effective for producing a beneficial or desired clinical result in at least a sub-population of cells in a subject at a reasonable benefit/risk ratio applicable to any medical treatment. For example, a therapeutically effective amount delivered to a target site or close proximity thereof, e.g., at least a portion of an eye (e.g., vitreous humor) and/or ocular cells (e.g., retinal cells) is sufficient to, directly or indirectly, produce a statistically significant, measurable therapeutic effect as defined herein. By way of example only, when an ocular condition to be treated is a poster segment ocular disease or condition (e.g., age-related macular degeneration), the therapeutically effective amount of nanoparticles delivered to at least a portion of an eye (e.g., vitreous humor) and/or ocular cells (e.g., retinal cells) is sufficient to reduce at least one symptom or marker associated with the posterior segment ocular disease or condition (e.g., age-related macular degeneration) by at least about 10%, at least about 20%, at least about 30%, at least about 40%, at least about 50%, at least about 60% or higher (but excluding 100%), as compared to absence of the nanoparticles or biologically active agents. In some embodiments, the therapeutically effective amount delivered to at least a portion of an eye (e.g., vitreous humor) and/or ocular cells (e.g., retinal cells) is sufficient to reduce at least one symptom or marker associated with the posterior segment ocular disease or condition (e.g., age-related macular degeneration) by at least about 60%, at least about 70%, at least about 80% or higher (but excluding 100%), as compared to absence of the nanoparticles or biologically active agent payload. In some embodiments, the therapeutically effective amount delivered to at least a portion of an eye (e.g., vitreous humor) and/or ocular cells (e.g., retinal cells) is sufficient to reduce at least one symptom or marker associated with the posterior segment ocular disease or condition (e.g., age-related macular degeneration) by at least about 80%, at least about 90%, at least about 95%, at least about 98%, at least about 99% or higher (but excluding 100%), as compared to absence of the nanoparticles or biologically active agent. In some embodiments, the therapeutically effective amount delivered to at least a portion of an eye (e.g., vitreous humor) and/or ocular cells (e.g., retinal cells) is sufficient to reduce at least one symptom or marker associated with the posterior segment ocular disease or condition (e.g., age-related macular degeneration) by 100%, as compared to absence of the nanoparticles or biologically active agent.

Determination of a therapeutically effective amount is well within the capability of those skilled in the art. Generally, a therapeutically effective amount can vary with, for example, the subject's history, age, condition, sex, as well as the severity and type of the medical condition in the subject, and/or administration of other pharmaceutically active agents. Furthermore, the therapeutically effective amounts can vary, as recognized by those skilled in the art, depending on the specific disease treated, the route of administration, the excipient selected, and the possibility of combination therapy, e.g., laser coagulation and/or surgery. In some embodiments, the therapeutically effective amount can be in a range between the ED50 and LD50 (a dose of a therapeutic agent at which about 50% of subjects taking it are killed). In some embodiments, the therapeutically effective amount can be in a range between the ED50 (a dose of a therapeutic agent at which a therapeutic effect is detected in at least about 50% of subjects taking it) and the TD50 (a dose at which toxicity occurs at about 50% of the cases). In alternative embodiments, the therapeutically effective amount can be an amount determined based on the current dosage regimen of the same biologically active agent administered without a nanoparticle. For example, an upper limit of the therapeutically effective amount can be determined by a concentration or an amount of the biologically active agent delivered to at least a portion of an eye, e.g., vitreous humor, on the day of administration with the current dosage of the biologically active agent without the nanoparticle; while the lower limit of the effective amount can be determined by a concentration or an amount of the biologically active agent delivered to at least a portion of an eye, e.g., vitreous humor, on the day at which a fresh dosage of the biologically active agent without a nanoparticle required.

As used herein, the term "maintain" is used in reference to sustaining a concentration or an amount of a biologically active agent delivered to a target site of an eye at least about or above the therapeutically effective amount over a specified period of time. In some embodiments, the term "maintain" as used herein can refer to keeping the concentration or amount of a biologically active agent at an essentially constant value over a specified period of time. In some embodiments, the term "maintain" as used herein can refer to keeping the concentration or amount of a biologically active agent within a range over a specified period of time. For example, the concentration or amount of a biologically active agent delivered to a target site of an eye can be maintained within a range between about the ED50 and about the LD50 or between about the ED50 and about the TD50 over a specified period of time. In such embodiments, the concentration or amount of a biologically active agent delivered to a target site of an eye can vary with time, but is kept within the therapeutically effective amount range for at least 90% of the specified period of time (e.g., at least about 95%, about 98%, about 99%, up to and including 100%, of the specified period of time).

In some embodiments, the biologically active agent is present in an amount sufficient to maintain a release or delivery of the biologically active agent from the nanoparticle to a target site of an eye or close proximity thereof, upon administration, at a therapeutically effective amount over a specified period of time, over a period of more than 1 month, including, e.g., at least about 2 months, at least about 3 months, at least about 6 months, at least about 12 months or longer. Such amounts of the biologically active agent dispersed or encapsulated in a nanoparticle can be generally smaller, e.g., at least about 10% smaller, than the amount of the biologically active agent present in the current dosage of the treatment regimen (i.e., without nanoparticle) required for producing essentially the same therapeutic effect. Indeed, a biologically active agent encapsulated in, or adhered to, a nanoparticle can potentially increase duration of the therapeutic effect for the biologically active agent. Stated another way, encapsulating a biologically active agent in a nanoparticle or adhering the agent to the nanoparticle can increase its therapeutic efficacy, i.e., a smaller amount of a biologically active agent encapsulated in a nanoparticle, as compared to the amount present in a typical one dosage administered for a particular ocular condition (e.g., age-related macular degeneration), can achieve essentially the same therapeutic effect. Accordingly, the nanoparticle can comprise the biologically active agent in an amount which is less than the amount traditionally recommended for one dosage of the biologically active agent, while achieving essentially the same therapeutic effect. For example, if the traditionally recommended dosage of the biologically active agent is X amount then the nanoparticle can comprise a biologically active agent in an amount of about 0.9X, about 0.8X, about 0.7X, about 0.6X, about 0.5X, about 0.4X, about 0.3X, about 0.2X, about 0.1X or less. Without wishing to be bound by the theory, this can allow administering a lower dosage of the biologically active agent in a nanoparticle to obtain a therapeutic effect which is similar to when a higher dosage is administered without the nanoparticle. Low-dosage administration of the biologically active agent can reduce side effects of the biologically active agent, if any, and/or reduce likelihood of the subject's resistance to the biologically active agent after administration for a period of time.

In some embodiments, an amount of the biologically active agent adhered to, or encapsulated within, the nanoparticle can be more than the amount generally recommended for one dosage of the same biologically active agent administered for a particular indication (e.g., age-related macular degeneration). Administration of a biologically active agent (e.g., triamcinolone acetonide or digoxin) in solution does not generally allow controlled and sustained release. Thus, release rate of a biologically active agent in solution can generally create a higher initial burst and/or overall faster release kinetics than that of the same amount of the biologically active agent loaded in a nanoparticle. Because of such higher initial burst observed in solution delivery, a current single dosage administered to an eye of a subject generally contains a limited amount of biologically active agent in solution, e.g., to ensure that the initial burst concentration does not go beyond the toxic level.

In some embodiments, where the biologically active agent is loaded in or on a nanoparticle at a high concentration, the biologically active agent can be first encapsulated into or on nanoparticle, which are then further embedded in a solid substrate and/or biomaterial.

In some embodiments, an amount of the biologically active agent encapsulated in or on the nanoparticle can be essentially the same amount generally recommended for one dosage of the biologically active agent, but providing a longer therapeutic effect.

In some embodiments, the nanoparticles of the invention provide sustained delivery of the biologically active agents encapsulated within, or adhered to the surface of, the nanoparticles. As used herein, the term "sustained delivery" refers to continual delivery of a biologically active agent in vivo or in vitro over a period of time following administration. For example, sustained release can occur over a period of at least about 1 day, 3 days, at least about a week, at least about two weeks, at least about three weeks, at least about four weeks, at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months or longer. In some embodiments, the sustained release can occur over a period of more than one month or longer. In some embodiments, the sustained release can occur over a period of at least about three months or longer. In some embodiments, the sustained release can occur over a period of at least about six months or longer. In some embodiments, the sustained release can occur over a period of at least about nine months or longer. In some embodiments, the sustained release can occur over a period of at least about twelve months or longer.

Sustained delivery of the biologically active agent in vivo can be demonstrated by, for example, the continued therapeutic effect (e.g., reducing at least one symptom associated with a posterior segment ocular disease or condition (e.g., age-related macular degeneration) of the biologically active agent over time. Alternatively, sustained delivery of the biologically active agent can be demonstrated by detecting the presence or level of the biologically active agent in vivo over time. By way of example only, sustained delivery of the biologically active agent, upon intravitreal administration, can be detected by measuring the amount of biologically active agent present in aqueous humor, vitreous humor and/or blood serum of a subject. The release rate and/or release profile of a biologically active agent can be adjusted by a number of factors such as nanoparticle composition and/or concentration, porous property (e.g., pore size and/or porosity) of the polymer membrane, amounts and/or molecular size of the biologically active agent loaded in a nanoparticle, and/or interaction of the biologically active agent with the nanoparticle (e.g., binding affinity of the biologically active agent to a polymer membrane), and any combinations thereof. For example, if the biologically active agent has a higher affinity with the polymer membrane, the release rate is usually slower than the one with a lower affinity with the polymer membrane. Additionally, when a polymer membrane has larger pores, the encapsulated biologically active agent is generally released from the polymer membrane faster than from a polymer membrane with smaller pores.

Compositions used in the methods of the invention can be formulated according to known methods for preparing pharmaceutically useful compositions. Formulations are described in a number of sources which are well known and readily available to those skilled in the art. For example, Remington's Pharmaceutical Sciences (Martin E W, 1995, Easton Pa., Mack Publishing Company, 19th ed.) describes formulations which can be used in connection with the subject invention. Formulations suitable for parenteral administration include, for example, aqueous sterile injection solutions, which may contain antioxidants, buffers, bacteriostats, and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. It should be understood that in addition to the ingredients particularly mentioned above, the formulations of the subject invention can include other agents conventional in the art having regard to the type of formulation in question.

The terms "subject", "patient", and "individual" are used interchangeably herein to refer to human or non-human animals to which the nanoparticles or compositions can be administered. In some embodiments, the subject is a human or non-human mammal. In some embodiments, the subject is a human. In some embodiments, the subject is a rodent such as a mouse or rat. In some embodiments, the subject is a rabbit.

The terms "comprising", "consisting of" and "consisting essentially of" are defined according to their standard meaning. The terms may be substituted for one another throughout the instant application in order to attach the specific meaning associated with each term.

The terms "isolated" or "biologically pure" refer to material that is substantially or essentially free from components which normally accompany the material as it is found in its native state or in which the material is formed.

As used in this specification, the singular forms "a", "an", and "the" include plural reference unless the context clearly dictates otherwise. Thus, for example, a reference to "a nanoparticle" includes more than one such nanoparticle.

EXEMPLIFIED EMBODIMENTS

Embodiment 1. A nanoparticle, comprising a core of a first biologically active agent encapsulated by a membrane of one or more polymers; and a second biologically active agent adhered to an outside surface of the membrane.

Embodiment 2. The nanoparticle of embodiment 1, wherein first biologically active agent is a drug.

Embodiment 3. The nanoparticle of embodiment 1 or 2, wherein the second biologically active agent is a drug.

Embodiment 4. The nanoparticle of any preceding embodiment, wherein the first biologically active agent or the second biologically active agent comprises an immunosuppressive agent that suppresses vascular endothelial growth factor (VEGF).

Embodiment 5. The nanoparticle of embodiment 4, wherein the immunosuppressive agent comprises a corticosteroid.

Embodiment 6. The nanoparticle of embodiment 5, wherein the immunosuppressive agent comprises triamcinolone or a derivative thereof.

Embodiment 7. The nanoparticle of embodiment 5, wherein the immunosuppressive agent comprises triamcinolone acetonide or a pharmaceutically acceptable salt thereof.

Embodiment 8. The nanoparticle of embodiment 5, wherein the immunosuppressive agent comprises loteprednol etabonate or a pharmaceutically acceptable salt thereof.

Embodiment 9. The nanoparticle of any preceding embodiment, wherein the first biologically active agent or the second biologically active agent inhibits hypoxia induced factor (HIF).

Embodiment 10. The nanoparticle of embodiment 9, wherein the agent that inhibits hypoxia induced factor comprises digitalis or a derivative thereof.

Embodiment 11. The nanoparticle of embodiment 10, wherein the agent that inhibits hypoxia induced factor comprises digoxin or a pharmaceutically acceptable salt thereof.

Embodiment 12. The nanoparticle of any preceding embodiment, wherein the first biologically active agent comprises an immunosuppressive agent that suppresses vascular endothelial growth factor (VEGF), and the second biologically active agent inhibits hypoxia induced factor (HIF).

Embodiment 13. The nanoparticle of any one of embodiments 1 to 11, wherein the first biologically active agent inhibits hypoxia induced factor (HIF), and wherein the second biologically active agent comprises an immunosuppressive agent that suppresses vascular endothelial growth factor (VEGF).

Embodiment 14. The nanoparticle of any preceding embodiment, wherein the one or more polymers are biocompatible and biodegradable.

Embodiment 15. The nanoparticle of any preceding embodiment, wherein the one or more polymers comprise poly(lactic-co-glycolic acid) (PLGA), poly lactic acid (PLA), poly caprolactone (PCL), or a combination of two or more of the foregoing Embodiment 16. A composition comprising nanoparticles of any one of embodiments 1 to 15; and a pharmaceutically acceptable carrier or diluent.

Embodiment 17. The composition of embodiment 16, wherein the composition is a fluid that may be administered to an eye by injection or dropwise.

Embodiment 18. A method for treating a posterior segment ocular disease or condition in an eye of a subject, comprising administering nanoparticles of any one of embodiments 1 to 15 to the ocular posterior segment of the eye, e.g., by intravitreal injection.

Embodiment 19. The method of embodiment 18, wherein the posterior segment ocular disease is macular degeneration or diabetic retinopathy.

Embodiment 20. The method of embodiment 18 or 19, wherein said administering comprises administering a composition comprising the nanoparticles and a pharmaceutically acceptable carrier or diluent.

Embodiment 21. The method of any preceding embodiment, wherein the nanoparticles or composition is administered by intravitreal injection.

Embodiment 22. A method for making a nanoparticle, the method comprising:

mixing a first biologically active agent, one or more polymers and one or more solvents to make an organic phase, wherein the organic phase is a solution or dispersion;

mixing water with one or more acids or one or more bases to make a first aqueous phase, mixing the organic phase with the first aqueous phase to make a colloidal suspension of nanoparticles; wherein the nanoparticles comprise a core of the first biologically active agent encapsulated by a membrane of the one or more polymers;

isolating the nanoparticles from the colloidal suspension;

mixing a second biologically active agent with water to make a second aqueous phase, and mixing the nanoparticles with the second aqueous phase to make the nanoparticle, wherein the nanoparticle comprises a core of the first biologically active agent encapsulated by a membrane of the one or more polymers and the second biologically active agent adhering to an outside surface of the membrane of the one or more polymers.

Embodiment 23. The method of embodiment 22, wherein first biologically active agent is a drug.

Embodiment 24. The method of embodiment 22 or 23, wherein the second biologically active agent is a drug.

Embodiment 25. The method of any preceding embodiment, wherein the first biologically active agent or the second biologically active agent comprises an immunosuppressive agent that suppresses vascular endothelial growth factor (VEGF).

Embodiment 26. The method of embodiment 25, wherein the immunosuppressive agent comprises a corticosteroid.

Embodiment 27. The method of embodiment 25, wherein the immunosuppressive agent comprises triamcinolone or a derivative thereof.

Embodiment 28. The method of embodiment 25, wherein the immunosuppressive agent comprises triamcinolone acetonide or a pharmaceutically acceptable salt thereof.

Embodiment 29. The method of embodiment 25, wherein the immunosuppressive agent comprises loteprednol etabonate or a pharmaceutically acceptable salt thereof.

Embodiment 30. The method of any preceding embodiment, wherein the first biologically active agent or the second biologically active agent inhibits hypoxia induced factor (HIF).

Embodiment 31. The method of embodiment 30, wherein the agent that inhibits HIF comprises digitalis or a derivative thereof.

Embodiment 32. The method of embodiment 30, wherein the agent that inhibits HIF comprises digoxin or a pharmaceutically acceptable salt thereof.

Embodiment 33. The method of any preceding embodiment, wherein the first biologically active agent comprises an immunosuppressive agent that suppresses vascular endothelial growth factor (VEGF), and the second biologically active agent inhibits hypoxia induced factor (HIF).

Embodiment 34. The method of any one of embodiments 22 to 33, wherein the first biologically active agent inhibits hypoxia induced factor (HIF), and wherein the second biologically active agent comprises an immunosuppressive agent that suppresses vascular endothelial growth factor (VEGF).

Embodiment 35. The method of any preceding embodiment, wherein the one or more polymers are biocompatible and biodegradable.

Embodiment 36. The method of any preceding embodiment, wherein the one or more polymers comprise poly(lactic-co-glycolic acid) (PLGA), poly lactic acid (PLA), poly caprolactone (PCL), or a combination of two or more of the foregoing Embodiment 37. The method of any preceding embodiment, wherein said isolating of the nanoparticles comprises centrifugation.

Embodiment 38. The method of any preceding embodiment wherein the nanoparticle releases about 75% to about 85% of the first biologically active agent in 20 hours, and releases about 15% to about 25% of the second biologically active agent in 20 hours.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1—Preparation of Dual Drug Delivery Nanoparticles

Triamcinolone acetonide (TA) and poly(lactic-co-glycolic acid) (PLGA) were mixed with acetone to make an organic phase, which was mixed with an organic phase, and the resulting nanoparticles were collected by centrifugation. Following production of the nanoparticles with the TA encapsulated therein, digoxin (DA), a digitalis derivative, was added by mixing the DA with water to make a second aqueous phase, and mixing the TA nanoparticles with the second aqueous phase to make the dual drug delivery. Each nanoparticle comprises a core of TA encapsulated by a membrane of PLGA and the DA adhering to the outside surface of the PLGA membrane.

Materials: Poly(lactic-co-glycolic acid) (PLGA) (PEG-PLGA) (50:50 Lactide Glycolide; M.W. 19,000) was purchased from Acros Organic (New Jersey, USA). Triamcinolone acetonide was purchased from Alfa Aesar (Ward Hill, Mass.). Thiazolyl blue tetrazolium bromide (MTT reagent), acetone and methanol were purchased from Sigma Aldrich (St. Louis, Mo.). All other chemicals used in the study were of analytical grade and were used without any further purification unless specified.

Nanoparticle preparation: TA NPs were prepared using the nanoprecipitation method (FIG. 1). Briefly, 22 mg of TA and 110 mg of PLGA were dissolved in 2 ml acetone (organic phase), and the resulting solution was added dropwise to 20 ml of alkaline water $P^H$ 9.0 spinning at 300 rpm overnight to allow the full evaporation of the organic phase and the formation of the NP suspension. The NPs were separated by centrifugation at 3000 rpm for 10 min and re-suspended in fresh deionized $H_2O$.

Further details concerning the methods utilized are provided in the Supplemental Information below:

Supplemental Information

Preparation of Digoxin (DIG) Nanoparticles (NPs):

27.5 mg of poly(lactic-co-glycolic acid)(PLGA) was combined with 5.5 mg of Digoxin within 2.0 mL of tetrahydrofuran (THF)

This suspension was then added dropwise to 2 mL of DI water at a pH of 9 and left to spin at 500 rpm for 24 hours Spinning was then increased to 850 rpm for an additional 24 hours The suspension was then placed into a 15 mL tube and centrifuged at 5,000 rpm for 15 minutes The supernatant was then removed and 5 mL of DI water was added and re-suspended Example 2—Evaluation of Dual Drug Delivery Nanoparticles The nanoparticles were characterized for particle size, encapsulation efficiency, in vitro drug release, cytotoxicity, and effect on VEGF secretion.

(i) Particle size: Particle size and polydispersity index (PDI) were analyzed through dynamic light scattering (DLS) using the DynaPro Plate Reader (Wyatt Technology, CA). The Blank NP has particle size of 114 nm with Poly Dispersiblity Index (PDI) of 0.334, The TA NP has particle size of 173.87 nm with PDI of 0.125. PDI value of below one confirmed the uniform distribution of the nanoparticles.

| Item | Diameter (nm) | PDI |
| --- | --- | --- |
| Blank NP | 114 | 0.334 |
| TA-NP | 173.866 ± 7.575 | 0.125 ± .0769 |

(ii) Encapsulation efficiency: A 0.70 mL sample of TA nanoparticles were centrifuged at 12,000 rpm for 5 minutes at room temperature. The supernatant was removed and replaced with 0.70 mL of methanol and the sample was stored at 4° C. overnight. The supernatant was diluted 1:2 in methanol, then analyzed via UV spectroscopy (λ=240 nm). By comparing this value to the absorbance of standard dilutions of TA in methanol, the drug content could be determined. The encapsulation efficiency of the nanoparticles was 26.30.

Encapsulation Efficiency Determination:

$$\% \ EE = \frac{\text{Measured TA in NPs}}{\text{Theoretical TA in NPs}} \times 100\%$$

| Measured TA | Theoretical TA | % EE |
| --- | --- | --- |
| 0.289 mg/mL | 1.1 mg/mL | 26.3% |

Figure 2:
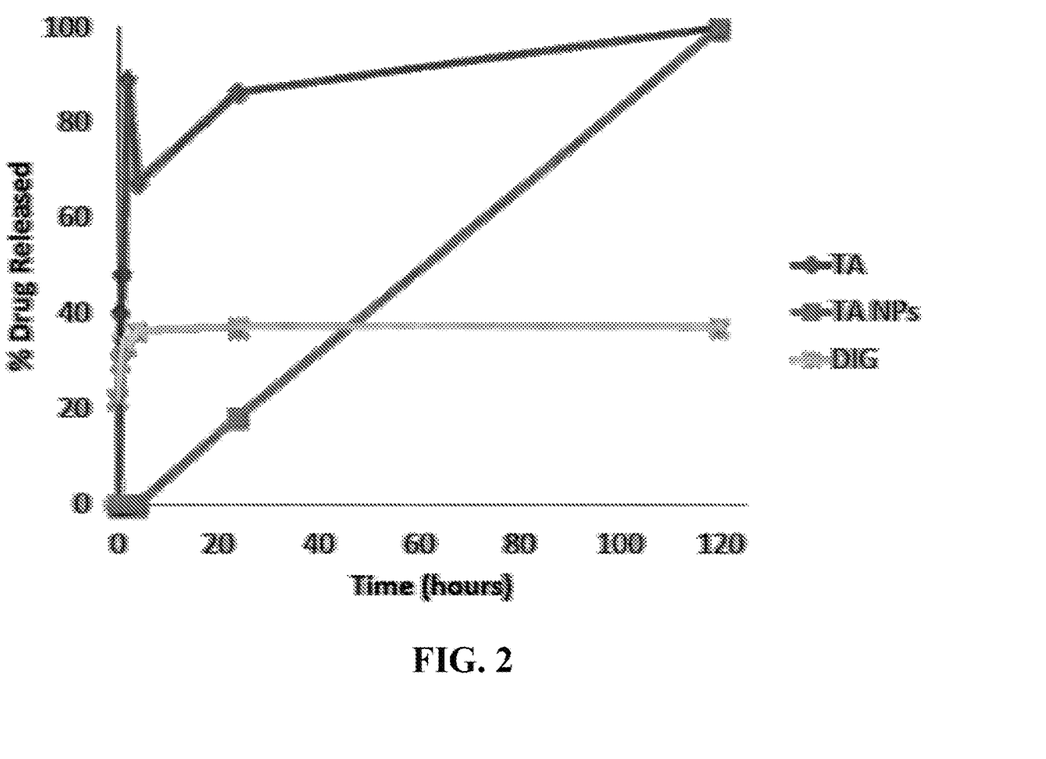
FIG. 2 is a graph showing results of an in vitro drug release test of the free triamcinolone acetonide (TA) solution, TA nanoparticles (TA NPs), and digoxin solution (DIG). Drug released (percentage) over time (hours) for triamcinolone acetate by itself (TA), versus digoxin by itself (DIG), and versus TA NPs is shown.
Figure 5:
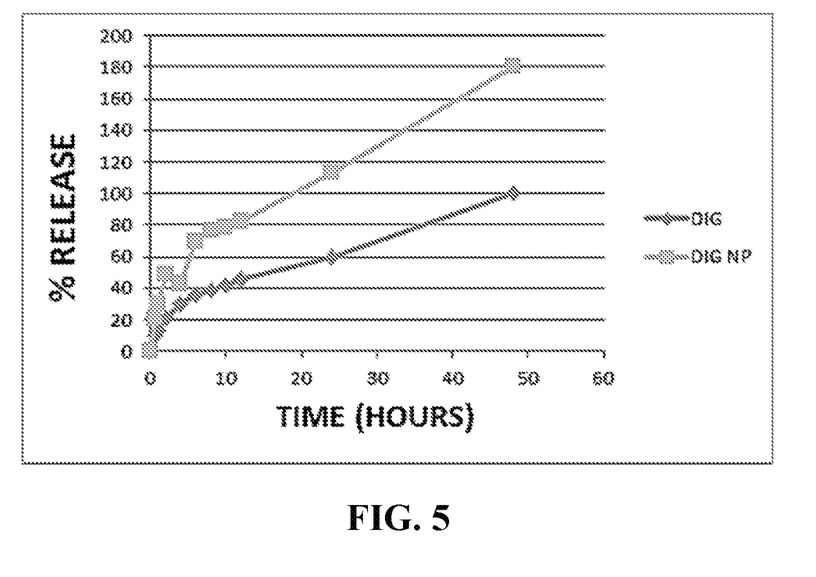
FIG. 5 is a graph showing results of an in vitro drug release study of the DIG solution and DIG nanoparticles (DIG NPs).

(iii) in vitro Drug Release: The rate of TA release from the NPs was measured by adapting a previously reported method. 40 Dialysis membrane tubing, MWCO 10 000 Da. (Spectrum Laboratories, Rancho Dominguez, Calif.) was soaked in deionized H2O overnight. 1 ml of the NP suspension was added to the dialysis membrane tubing after being briefly sonicated and was placed into 100 ml of PBS covered and stirring at 100 rpm at 37° C. 1 mL samples were removed at predetermined intervals over 10 days and replaced with fresh PBS. Samples were analyzed using UV spectroscopy at a wavelength of 240 nm (max) and compared to standard dilutions of TA in PBS ($r^2$=0.989) to determine the percentage of drug released over 10 days. Results are shown in FIGS. 2 and 5.

Figure 3:
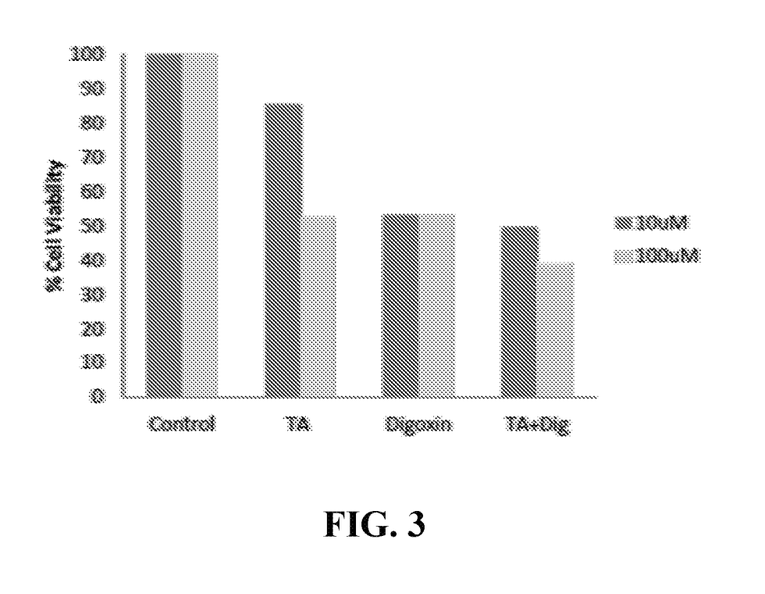
FIG. 3 is a graph showing results of an in vitro cytotoxicity study of TA solution, DIG solution, and TA+DIG combination solution. Percentage cell viability following treatment with 10 µM or 100 µM TA solution, DIG solution, and a combination of TA and solution, relative to control, is shown (control=untreated culture media).
Figure 6:
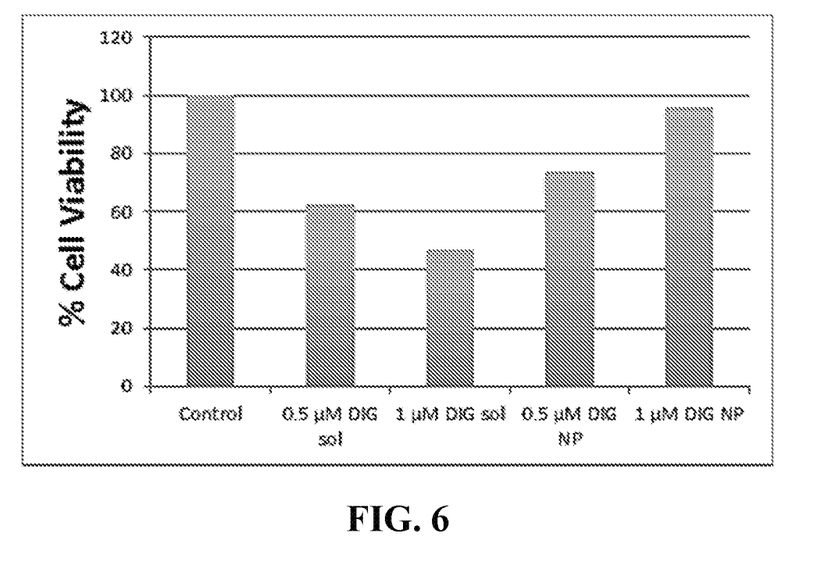
FIG. 6 is a graph showing results of a cytotoxicity study of the DIG nanoparticles (DIG NPs) versus DIG solution (SOL).

(iv) Cytotoxicity: The cytotoxicity of the TA Nanoparticles was assessed in ARPE-19 cells (cells of a human retinal pigment epithelial cell line) by the 3-(4,5-dimethyl-thiazol-2-yl)-2,5-diphenyltetrazolium bromide salt (MTT) assay. Briefly, cells were seeded in 24-well plates at a density of $5\times10^4$ cells/ml for 24 h to achieve confluency before treatment. Cells were exposed to free TA, Digoxin and TA+Digoxin solution (10, 100 μM) for 24 hours after which the MTT assay was performed. Cell culture media were aspirated, and 500 ml of MTT reagent solution (1 mg/ml) was added to each well. Cells were incubated at 37° C. and 5% CO2 for 4 h, after which the MTT reagent solution was aspirated and 1 mL of DMSO was added to each well. Plates were allowed to shake gently for 10 min before being read by Synergy H4 plate reader (Biotek Industries, Inc., Winooski, Vt.) at absorbance of 570 nm. Results are shown in FIGS. 3 and 6.

Figure 4:
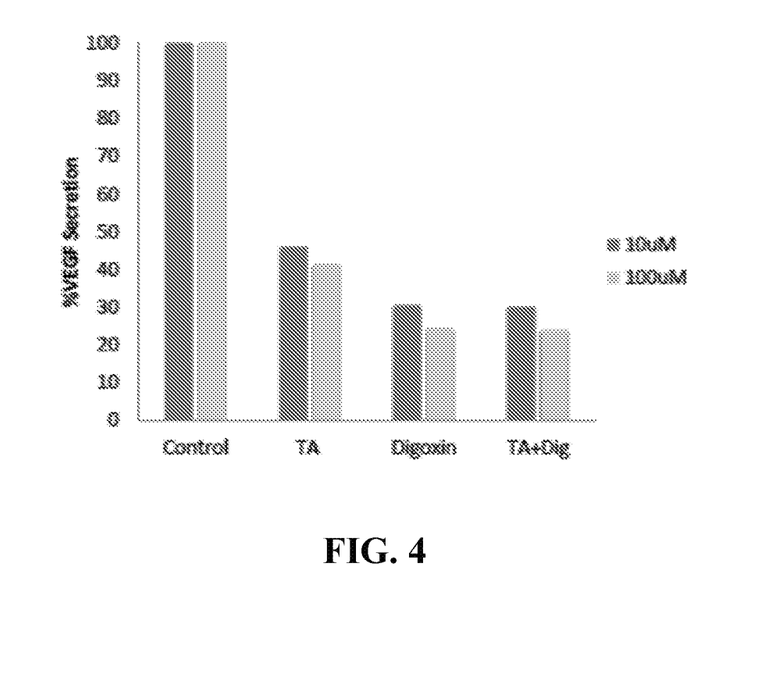
FIG. 4 is a graph showing the results of VEGF expression-ELISA studies of TA solution, DIG solution, and TA+DIG combination solution. Percentage VEGF expression following treatment with 10 µM or 100 µM TA solution, DIG solution, and a combination of TA and DIG (TA+DIG), relative to control, is shown (control=untreated culture media).

(v) VEGF secretion: ARPE-19 cells were seeded onto 24-well plates at $5\times10^4$ cells/ml and allowed to grow until confluence. On the day of study, cell culture media were replaced with 1% FBS experimental media and allowed to remain in quiescence for 12 hours. The cellular monolayers were incubated with varying treatment concentrations of free TA, Digoxin and TA+Digoxin solution (10, 100 μM). Culture media were collected at 12 and 72 hours. Secreted VEGF in collected culture media was quantified by the ELISA method (Human VEGFA ELISA kit, Thermo Scientific, Waltham, Mass.). The cell protein content was assayed using the BCA protein assay kit after lysing the cells, and VEGF secretion was normalized to total protein. Samples were read using the Synergy H4 plate reader (Biotek Industries, Inc., Winooski, Vt.) with absorbance at 450 nm minus absorbance at 550 nm. Results are shown in FIG. 4.

Figure 7:
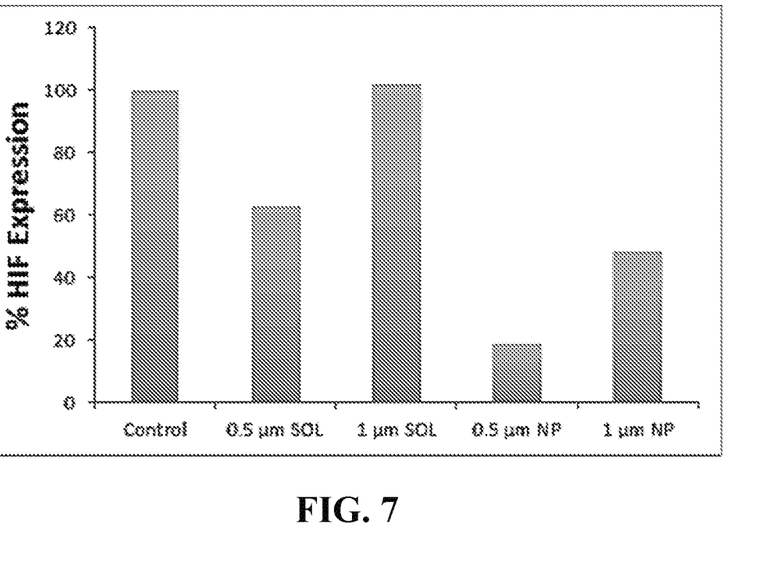
FIG. 7 is a graph showing results of HIF Expression-ELISA studies of the DIG solution (SOL) and DIG nanoparticles (NPs).

The present study showed that digoxin is able to provide a sustained therapeutic release with relatively low cell toxicity. Digoxin showed an increase in HIF suppression (FIG. 7), making it a viable candidate as a therapeutic agent for the treatment of AMD.

Further details concerning the methods utilized are provided in the Supplemental Information below:

Supplemental Information

Encapsulation Efficiency Preparation:

800 mL sample of the DIG NPs was taken and placed into a 1.5 mL tube

The sample was then centrifuged at 12,000 rpm for 5 minutes
The supernatant was removed and 800 mL of MeOH was added and re-suspended
Read using Synergy H4 at wavelength 230 nm at a temperature of 24.8° C.
Results showed an EE of 17.9%
NP Size and Polydispersity:
The particle size and polydispersity index (PDI) was determined by dynamic light scattering PDI less than 1 demonstrates uniform distribution
Approximate diameter of PLGA blank is 114 nm
Approximate PDI of PLGA blank is 0.334
In Vitro Drug Release:
20 mL PBS @ 40° C.
500 µL of 1 mg/mL DIG sol and 500 µL of DIG NPs in (cellulose) dialysis membrane tubing
Samples were taken in 750 µL increments and the respective amount of PBS was re-added
Cell Studies:
The cytotoxicity of Digoxin was determined through MTT assay and the suppression of HIF was determined via ELISA.
Media was removed and cells were washed with 500 µL of HBSS prior to treatment.
ELISA
Cells were placed into hypoxic conditions prior to treatment via cobalt II chloride hexahydrate ($CoCl_2$).
(2 µL of $CoCl_2$+498 µL Experimental Media *aspirated prior to treatment 24 hours later*)
*($CoCl_2.6H_2O$, MW=237.9) is a chemical inducer of hypoxia-inducible factor-1.3 8. This product is soluble in water (100 mg/ml)*
Cell treatments
   3 control wells with 500 µL Experimental Media only
   3 wells with DIG sol at 0.5 µM and 1 µM concentrations: (0.5 µM: 9.76 µL DIG sol+490.24 µL Exp. Media)
   (1 µM: 19.52 µL DIG sol+480.48 µL Exp. Media)
   3 wells with DIG NPs at 0.5 µM and 1 µM concentrations: (0.5 µM: 1.012 µL DIG NPs+499.98 µL Exp. Media)
   (1 µM: 2.024 µL DIG NPs+497.97 µL Exp. Media)
MTT Cell treatments: same as above w/o $CoCl_2$ step
MTT Assay:
Prepare MTT reagent: 0.5 mg/mL (in basal media) and cover with aluminum foil
Remove media from each well and wash with HBSS
Add 0.3 mL (300 µL) MTT solution and incubate for 4 hours (5% $CO_2$ at 37° C.)
After incubation remove reagent
Add 0.3 mL DMSO
Shake plate for 20 minutes at ~50 rpm
Read at 570 nm
HIF Expression—ELISA:
Add 50 µL of standards to each well
Cover plate and shake for 2 hours at room temperature
Wash plate three times; Add 50 µL of biotinylated HIF detection antibody
Cover plate and shake for 1 hour at room temperature
Wash plate three times; Add 50 µL of prepared Streptavidin-HRP to each well
Cover plate and shake for 30 minutes
Wash plate three times; Add 100 µL of TMB substrate
Develop plate in the dark at room temperature for 30 minutes
Add 100 µL of Stop Solution
Measure absorbance at 450 nm minus 550 nm
VEGF Expression—ELISA:
Add 50 µL of standards to each well
Cover plate and shake for 2 hours at room temperature
Wash plate three times; Add 50 µL of biotinylated VEGF detection antibody
Cover plate and shake for 1 hour at room temperature
Wash plate three times; Add 50 µL of prepared Streptavidin-HRP to each well
Cover plate and shake for 30 minutes
Wash plate three times; Add 100 µL of TMB substrate
Develop plate in the dark at room temperature for 30 minutes
Add 100 µL of Stop Solution
Measure absorbance at 450 nm minus 550 nm It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. A dual activity nanoparticle comprising:
   (a) a core comprising an immunosuppressive agent that suppresses vascular endothelial growth factor (VEGF) encapsulated by a membrane of one or more polymers comprising poly(lactic-co-glycolic acid) (PLGA), poly lactic acid (PLA), poly caprolactone (PCL) or combinations thereof; and a hypoxia induced factor (HIF) inhibitor adhering to an outside surface of the membrane of the one or more polymers; or
   (b) a core of a HIF inhibitor encapsulated by a membrane of one or more polymers comprises poly(lactic-co-glycolic acid) (PLGA), poly lactic acid (PLA), poly caprolactone (PCL) or combinations thereof, and an immunosuppressive agent that suppresses VEGF adhered to an outside surface of the membrane of the one or more polymers, wherein the immunosuppressive agent that suppresses VEGF is selected from the group consisting of triamcinolone acetonide or a pharmaceutically acceptable salt thereof, and loteprednol etabonate or a pharmaceutically acceptable salt thereof.

2. The dual activity nanoparticle of claim 1, wherein the nanoparticle has an average diameter of about 100 to 200 nm.

3. The dual activity nanoparticle of claim 1, wherein the nanoparticle has an average diameter of about 173-174 nm.

4. The dual activity nanoparticle of claim 1, wherein the membrane is a combination of two or more polymers comprising poly(lactic-co-glycolic acid) (PLGA), poly lactic acid (PLA), poly caprolactone (PCL) or combinations thereof.

5. The dual activity nanoparticle of claim 1, wherein the polymer is poly(lactic-co-glycolic acid) (PLGA).

6. The dual activity nanoparticle of claim 1, wherein the nanoparticle releases about 75% to about 85% of VEGF immunosuppressive agent of (a) or the HIF inhibitor of (b) in 20 hours.

7. The dual activity nanoparticle of claim 1, wherein the nanoparticle releases about 15% to about 25% the HIF inhibitor of (a) or VEGF immunosuppressive agent of (b) in 20 hours.

8. The dual activity nanoparticle of claim 1, wherein the VEGF immunosuppressive agent and/or the HIF inhibitor of either (a) or (b) are comprised in the nanoparticle in an amount which is less than the amount traditionally recommended for one dosage of the VEGF immunosuppressive agent and/or the HIF inhibitor, while achieving the same therapeutic effect.

9. The dual activity nanoparticle of claim 1, wherein the VEGF immunosuppressive agent and/or the HIF inhibitor of either (a) or (b) are comprised in the nanoparticle in an amount which is more than the amount traditionally recommended for one dosage of the VEGF immunosuppressive agent and/or the HIF inhibitor administered for a particular indication.

10. The dual activity nanoparticle of claim 1, wherein the VEGF immunosuppressive agent and/or the HIF inhibitor of either (a) or (b) are comprised in the nanoparticle in an amount which is essentially the same amount generally recommended for one dosage of the VEGF immunosuppressive agent and/or the HIF inhibitor administered but providing a longer therapeutic effect that the VEGF immunosuppressive agent and/or HIF inhibitor without the nanoparticle.

11. The dual activity nanoparticle of claim 1, wherein the nanoparticle provides sustained delivery of the VEGF immunosuppressive agent and/or the HIF inhibitor of either (a) or (b) encapsulated within, or adhered to the surface of, the nanoparticle.

12. The dual activity nanoparticle of claim 1 further comprising an additional biologically active agent.

13. The dual activity nanoparticle of claim 12, wherein the biologically active agent is incorporated into or onto the nanoparticle.

14. The dual activity nanoparticle of claim 13, wherein the biologically active agent is encapsulated within the polymer membrane of the nanoparticle or adhered to the membrane of the nanoparticle, or both.

15. A composition comprising the dual activity nanoparticles of claim 1, and a pharmaceutically acceptable carrier or diluent.

16. The dual activity nanoparticle of claim 1, wherein the VEGF immunosuppressive agent of (a) or the HIF inhibitor of (b) is a small molecule drug of less than 900 daltons.

17. The dual activity nanoparticle of claim 1, wherein the HIF inhibitor of (a) or VEGF immunosuppressive agent of (b) is a small molecule drug of less than 900 daltons.

18. A method for making a dual activity nanoparticle, the method comprising:
mixing a first biologically active agent, one or more polymers and one or more solvents to make an organic phase, wherein the organic phase is a solution or dispersion;
mixing water with one or more acids or one or more bases to make a first aqueous phase,
mixing the organic phase with the first aqueous phase to make a colloidal suspension of nanoparticles; wherein the nanoparticles comprise a core of the first biologically active agent encapsulated by a membrane of the one or more polymers;
isolating the nanoparticles from the colloidal suspension;
mixing a second biologically active agent with water to make a second aqueous phase, and
mixing the nanoparticles with the second aqueous phase to make the nanoparticle, wherein the nanoparticle comprises a core of the first biologically active agent encapsulated by a membrane of the one or more polymers and the second biologically active agent adhering to an outside surface of the membrane of the one or more polymers,
wherein the first biologically active agent is a VEGF immunosuppressive agent and the second biologically active agent is a HIF inhibitor or the first biologically active agent is a HIF inhibitor and the second biologically active agent is a VEGF immunosuppressive agent,
wherein the VEGF immunosuppressive agent selected from the group consisting of triamcinolone acetonide or a pharmaceutically acceptable salt thereof and loteprednol etabonate or a pharmaceutically acceptable salt thereof, and
wherein the one or more polymers comprise poly(lactic-co-glycolic acid) (PLGA), poly lactic acid (PLA), poly caprolactone (PCL) or combinations thereof.

19. The method of claim 18, wherein the first biologically active agent is a VEGF immunosuppressive agent and the second biologically active agent is a HIF inhibitor.

20. The method of claim 18, wherein the first biologically active agent is a HIF inhibitor and the second biologically active agent is a VEGF immunosuppressive agent.

* * * * *